United States Patent [19]

Komamura et al.

[11] 4,094,313
[45] June 13, 1978

[54] INTRA-UTERINE DEVICE AND TOOL FOR INSERTION OF SAME

[76] Inventors: Takeo Komamura, 4-9-11 Nishigahara, Kitaku, Tokyo; Tadao Okamoto, 1-12-8 Kohinata, Bunkyoku; Atsumi Ishihama, 3-6-30 Kagano, Morioka, all of Japan

[21] Appl. No.: 737,017

[22] Filed: Oct. 29, 1976

[30] Foreign Application Priority Data

Jun. 13, 1975 Japan .............................. 50-79399[U]
Jul. 16, 1975 Japan .......................... 50-5097816[U]

[51] Int. Cl.² ................................................ A61F 5/46
[52] U.S. Cl. .................................................... 128/130
[58] Field of Search ............................... 128/127–130, 128/260

[56] References Cited

U.S. PATENT DOCUMENTS

| | | | |
|---|---|---|---|
| D. 241,078 | 8/1976 | Okamoto et al. | 128/130 X |
| 3,794,025 | 2/1974 | Lerner | 128/130 |
| 3,918,445 | 11/1975 | Okamoto et al. | 128/130 |

Primary Examiner—Lawrence W. Trapp
Attorney, Agent, or Firm—Ralph W. Kalish

[57] ABSTRACT

An intrauterine device constructed of a flexible plastic and comprising a stem having adjacent one end a plurality of arms or branches extending laterally therefrom and being biased slightly in a direction toward the opposite end; the planes of said arms being at an angle of less than 90° to the plane of the stem and said arms being flexible about their juncture of engagement to said stem for bending toward or opposite the remote end thereof. Said stem remote from said arms is relatively thin and elongated and with there being a hook in its said remote end extremity. A tool for inserting said device is provided having a chamber for accepting the thin elongated portion of said device and finger-like guides embracingly engaging opposite sides of said stem between arms thereof and having its device engaging portion formed on a radius for promoting facile disengagement from the device upon limited longitudinal tilting of the tool when the device is in operative position.

13 Claims, 8 Drawing Figures

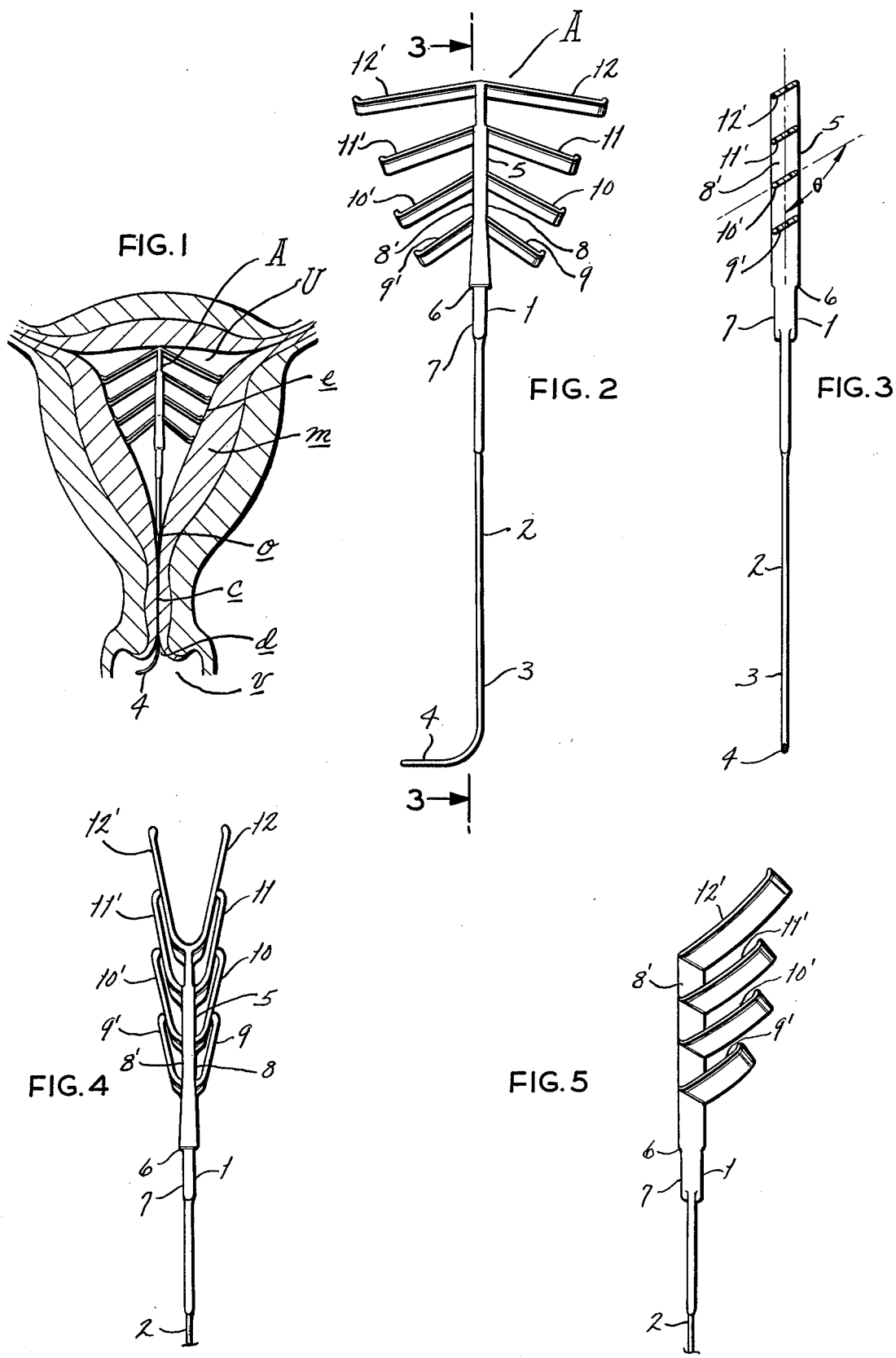

INTRA-UTERINE DEVICE AND TOOL FOR INSERTION OF SAME

BACKGROUND AND SUMMARY OF THE INVENTION

This invention relates in general to contraceptives and, more particularly, to certain new and useful improvements in an intrauterine device and a tool for inserting same.

Heretofore various intrauterine devices for conception control have been known and which have been generally of two basic types; one relying upon pharmacological properties for contraception, and the other being devoid of pharmacological properties and relying upon a physical relationship with the uterus. Within the former category certain devices have been adapted to emit hormones, while others have incorporated copper for bringing about an interreaction with the uterine wall. The present invention falls within the second class and thus being devoid of reacting in a pharmacological sense with the uterus.

With non-pharmacological active uterine devices the fundamental effort has been to effect a relatively increased contact between the devices and the uterine endometrium which may be achieved by direct engagement, as well as by the provision of means for covering relatively wide zones of the endometrium, such as through the medium of wires or networks. However, it is manifest that the quality of the contact between the devices and the endometrium is of extreme criticality so as to avoid any injury to the uterine wall with the potential for infection. Accordingly, effective, but limited contact of a non-injurious nature is desired.

In addition to the structure of the device itself there is always the problem of providing means, such as by a tool or implement, for effecting insertion of the device within the uterus. Accordingly, in addition to the desired characteristics of the device for bringing about contraception, the passage of the same through the cervical canal must be considered to prevent insult to the tissues. Certain devices heretofore known have been of tubular character for relatively facile insertion within the cervical canal and permitting the intrauterine device to be moved through the tube as by a plunger for expulsion into the uterus. Other efforts have involved the detachable mounting of a device upon the inner end of an inserting bar so that release may be effected upon withdrawing of the bar from the canal. With the tubular tool the intrauterine devices have been consistently formed of a relatively hard plastic which have with undesired frequency caused a piercing of the uterine wall upon expulsion. With the more readily detachable types of uterine devices the same have consistently caused a relative expansion of the cervical canal for insertion which in addition to causing discomfort has also brought about injury to the canal as well as to the external uterine orifice.

The present invention comprehends an intrauterine device which is formed of relatively soft, limitedly flexible plastic and incorporating a stem having a plurality of parallel branches or arms of decreasing extent projecting from the stem at a predetermined angle which branches or arms though inherently biased outwardly may be folded snugly inwardly toward the stem during inserting movement through the cervical canal and being easily reversely bent for promoting smooth, non-discomfort withdrawal through the canal. The said arms assure of sufficient contact with the uterine wall to inhibit implantation of a fertilized ovum within the uterus endometrium and thereby promote the expulsion of the same.

The present invention also contemplates a tool for inserting the intrauterine device of the present invention which is uniquely designed for maintaining the device in appropriate attitude during the insertion and being of such character as to substantially eliminate any harm or other adverse side effects to the walls of the cervical canal.

Therefore, it is an object of the present invention to provide an intrauterine device which may be easily inserted within, and withdrawn from, the uterus without being productive of injury to the uterus or cervical canal.

It is another object of the present invention to provide an intrauterine device of the character stated which is formulated of relatively flexible material, but incorporating components inherently urged into engagement with the uterine endometrium whereby the device is maintained in operative condition at all times during usage for effectively inhibiting contraception.

It is another object of the present invention to provide an intrauterine device of the character stated which is adapted for minimal contact with the uterine wall so as to relatively diminish any potential for irritation or the like of the wall.

It is a still further object of the present invention to provide an intrauterine device of the character stated which will maintain operative condition over long periods of time without undesired deformation or displacement.

It is another object of the present invention to provide an intrauterine device of the character stated which is adapted for facile withdrawal from the uterus without requiring the utilization of invasive instruments.

It is also another object of the present invention to provide an instrument for inserting the intrauterine device which is adapted for easily detachable engagement with the device to assure requisite retention during inserting and ease of removal from the device when engaged within the uterus.

It is a further object of the present invention to provide an instrument of the type shown which is easily manipulable for effecting operative placement of the device and for disengaging same.

It is another object of the present invention to provide an intrauterine device of the character stated which is most economically manufactured and which is reliable and durable in usage; and being so cheaply produced to be patently of discardable character.

It is another object of the present invention to provide an instrument for the purpose stated which is economically manufactured of durable material and being uniquely designed for requisite relationship with the intrauterine device.

BRIEF DESCRIPTION OF THE DRAWINGS

FIG. 1 is a vertical sectional view of the uterus having disposed therein, in operative position, an intrauterine device constructed in accordance with and embodying the present invention.

FIG. 2 is a front view of the intrauterine device.

FIG. 3 is a vertical transverse sectional view taken on the line 3—3 of FIG. 2.

FIG. 4 is a front view of the intrauterine device but with the branches or arms being reversely bent in withdrawing position.

FIG. 5 is a side view.

DESCRIPTION OF THE PREFERRED EMBODIMENTS

Figure 6:
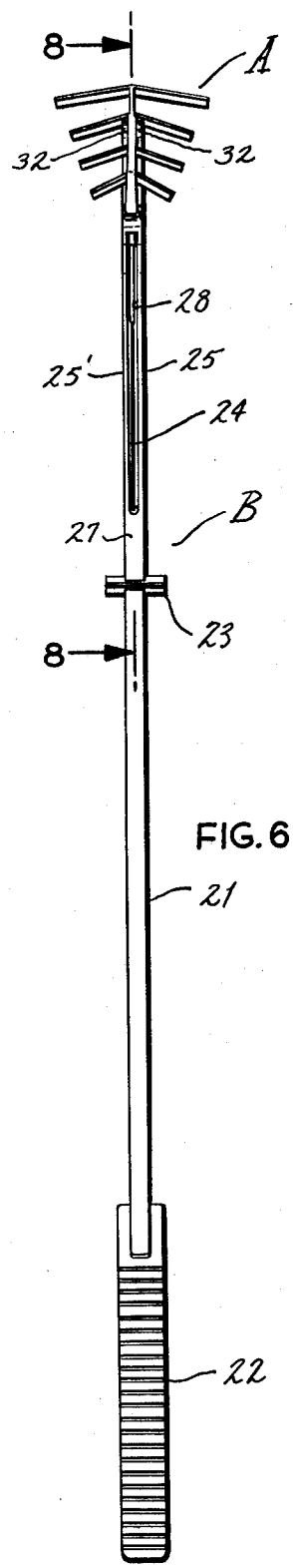
FIG. 6 is a front view of an intrauterine inserting tool constructed in accordance with and embodying the present invention illustrating same with an intrauterine device engaged thereon in inserting disposition.

Referring now by reference numerals to the drawings which illustrate preferred embodiments of the present invention, A generally designates an intrauterine device preferably of a molded flexible plastic having a central elongated stem 1 which in its normally lower end portion 2 is of relatively reduced diameter so as to provide a generally thread-simulative section 3 having a short hook forming a terminal 4 substantially axially perpendicular to section 3. The upper portion of stem 1 is of substantially greater thickness than thread portion 3, as at 5, incorporating a shoulder 6 constituting the upper limit of a section 7 between upper and lower portions 5,2, respectively, and being of intermediate thickness with respect thereto. Said upper portion 5 comprehends planar parallel side walls 8,8' from each of which laterally project in opposite directions a plurality of arms or branches 9, 10, 11, 12 and 9', 10', 11', 12', respectively; the arms projecting from stem side wall 8 corresponding to, and being symmetrical with, the related arms extending from side wall 8'. Arms 12,12' which are located at the upper end of device A are of greater length than the adjacent arms 11,11' which, in turn, slightly exceed the length of arms 10,10', and which latter correspondingly are of greater extent than arms 9,9'; whereby an outward diverging edge contour is developed by the arms as one progresses from forward-most arms 9,9' to outer arms 12,12'. Such relationship thus presents an edge conformity to the diverging nature of the uterus, as at U in FIG. 1, wherein e designates the endometrium and the myometrium is indicated m, as the same proceeds upwardly from the interior uterine orifice o (see FIG. 1). The spacing between the adjacent arms is substantially uniform from utilitarian as well as economic standpoints although such spacing is not crucial since the disposition of the arms or branches 9,9' – 12,12' is dictated by the need to effect requisite engagement of the outer ends thereof with the uterine endometrium e. Each of the aforesaid arms or branches are axially flexible about their engagement with stem 1 as to be easily bendable in reverse directions for purposes appearing more fully hereinbelow.

With reference being made particularly to FIG. 3 it will be seen that the arms or branches 9,9' through 12,12', inclusive, are inherently biased so that their longitudinal axes form an angle of less than 90° with the axis of stem 1 whereby such axes normally project laterally and downwardly. By reason of the inherent slight downward bias of said arms or branches and in view of their flexibility, the same are readily bent or folded inwardly in the general direction toward stem 1 as the intrauterine device is introduced into the confining wall of the human cervical canal c (see FIG. 1) and held by such wall during transit therethrough so that negligible, if any, discomfort is accorded the individual during insertion. As the intrauterine device passes through the interior uterine orifice o and thus introduced into the upwardly expanding or diverging uterus U the arms or branches commencing from the upper end of device A are progressively freed from the restriction embodied by the cervical canal c and, thus, allowed to return to normal bias condition as shown in FIG. 3.

The overall length of each arm 9,9' – 12,12', inclusive, is slightly greater than the minimum distance between upper stem portion 5 and the proximate zone of the intrauterine wall so that the said arms or branches in their normally biased condition will cause their outer end edges to make firm, but non-injurious, contact with the uterine wall and thereby through such engagement be securely retained in operative position.

It is to be further particularly noted that the line of integration or jointure of each arm or branch 9,9' – 12,12' with stem portion 5 is at an angle of less than 90° to the longitudinal axis of stem portion 5, such angle being indicated at $\angle \theta$ in the drawings (see FIG. 3), and being within the range of approximately 30° to 50°. This angulation is productive of an enhanced stabilization of the device in operative position, resisting any tendency of the device to twist, tilt, or become distorted, as well as to be displaced vertically, so as to effect a loss of contact with one or more of the arms of the uterine wall or to provide an unbalanced engagement. This angle presents a marked advance in the art, assuring of efficacious retention of the device in operative position. The novel angular relationship of the arms or branches to the stem conduces to relatively less inhibited menstrual flow than was occasioned by devices incorporating arms extending perpendicularly from a central portion and furthermore the inclusion of the stated angle has been found to permit of a reduced thickness of such arms or branches without any diminution in strength or effectiveness for both insertion and withdrawal purposes as well as retentiveness in engaged condition. The permitted relative slenderization of such arms or branches brings about a still further unusual result and that is in enhancing the sensitivity of such arms or branches to the normal continuous flexing or alternate contractile and expanding action of the uterus U so that on contracting said arms or branches are correspondingly flexed inwardly and upon expansion of such wall said arms return outwardly whereby requisite contact is at all times maintained without injury to the uterus U and without displacement of device A.

By reference to FIG. 1 it will be seen that lower stem portion 2 is of such length that when device A is in mounted condition, terminal 4 will be located within the vagina v downwardly of the external uterine orifice d for ready accessibility for purposes of withdrawal of device A.

Referring to FIG. 4 it will be seen that when device A is withdrawn from uterus U as by being pulled through canal c by the application of a pulling force upon hook 4, arms or branches 9,9' – 12,12' will be progressively subjected to a restricting path through the uterus as device A follows the downwardly tapering nature of the walls thereof causing said arms and branches to be folded or bent in what may be considered an upward condition as suggested in FIG. 4 and with such folding being further increased as device A transits canal c. Thus the relative thickness and flexibility of said arms and branches permits same to readily assume such reversely folded condition and present an overall compact relationship to permit of a smooth facile passage through canal c with negligent, if any, discomforting contact with the canal walls. Thereby device A is uniquely contrived to allow for quick, easy, and noninjurious removal.

Figure 7:
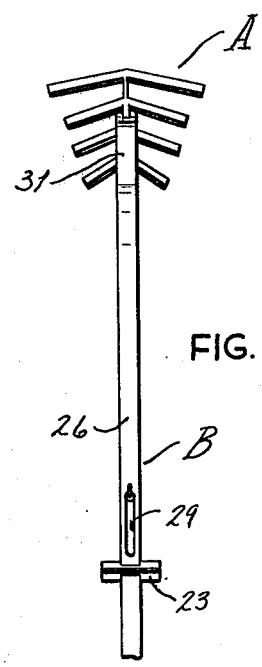
FIG. 7 is a partial bottom plan view of the tool.
Figure 8:
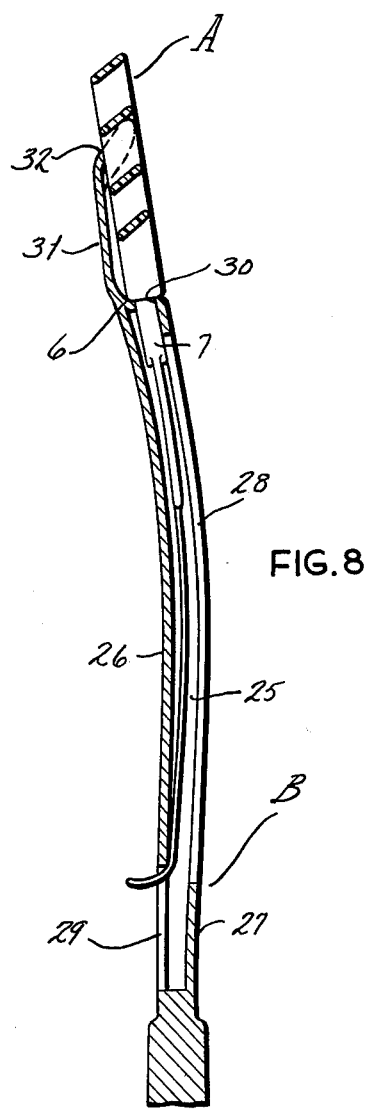
FIG. 8 is a vertical transverse sectional view taken substantially on the line 8—8 of FIG. 6.

Turning now to FIGS. 6, 7 and 8, B designates a tool or instrument for insertion of device A and comprises an elongated narrow rigid body 21 fabricated of metal, such as stainless steel or the like, and having an enlarged handle 22 at its outer or lower end. Spacedly from the opposite end of said tool B there is an integral, relatively short cross piece 23 perpendicular to the axis of said tool A which cross piece 23 is so located as to limit the extent of insertion of tool A being engageable with the upper vaginal wall adjacent external uterine orifice d so that any further insertion is effectively inhibited, although as will be shown hereinbelow said cross piece is presented merely for precautionary purposes as the distance between same and the proximate end of tool B is such that in normal operation said cross piece will be disposed spacedly below the upper vaginal wall. Forwardly of cross piece 23 tool B is hollowed to provide a continuous elongated chamber 24 which is defined by side walls 25,25', a base 26, and a top wall 27. Said top wall 27 is cut away throughout the major portion of its length to define a slot-like opening 28 communicating with chamber 24 and with base 26 being provided in its rearwardmost portion with a narrow opening 29 of limited extent which latter is longitudinally offset from opening 28. At its forward end chamber 28 communicates with the normally inner or forward end of tool B through an end aperture 30 which latter has a diameter of but slightly greater extent than that of intermediate stem portion 7 of device A for purposes presently appearing. In its forward or inner portion base wall 26 is continuous with a tongue-like extension 31 at the extremity of which are provided a pair of laterally spaced apart upwardly projecting guides or fingers 32 defining a path therebetween substantially equal to the thickness of upper stem portion 5. As may best be seen in FIG. 8 the upper end portion of tool B. that is, upwardly of cross piece 23, is formed on a slight radius or curvature within the plane of body portion 21 so that when tool B is disposed in horizontal disposition, tongue 31 and the adjacent upper or inner end of tool B will project slightly downwardly of section B for purposes presently appearing.

In actual use, device A is disposed upon tool B in the following manner: — the thread-simulative section 3 is directed through aperture 30 and then directed along chamber 24 with said device being suitably manipulated so as to feed hook 4 through opening 29 as into the position shown in FIGS. 7 and 8. Said hook 4 will thus abut against the adjacent edge of opening 29. As pointed out above intermediate stem portion 7 of device A is of substantially like diameter as aperture 30 for relatively snug acceptance therein and with further longitudinal movement of device A relative to tool B inhibited by abutment of shoulder 6 against the inner or forward end of tool B surrounding opening 30. Tongue 31 is of such length that guides 32 will snugly receive stem upper portion 5 as between arms 11,11' and 10,10' and being of sufficient extent so as to contact the adjacent arms and thereby further stabilize device A in engaged condition upon tool B.

It will thus be seen that device A and tool B are uniquely coordinated so that device A is sufficiently securely retained by tool B to permit of suitable manipulation of the latter for device-inserting purposes without danger of accidental or premature displacement of device A therefrom. It should be particularly noted that the combined length of device A as engaged by tool B and the outer or cross piece adjacent extremity of opening 29 is slightly greater than the normal distance between the upper wall of the uterus U and the external uterine orifice d so that said stem hooked portion 4 will be presented immediately below said orifice d for ready accessibility.

The operation of tool B should be apparent from the foregoing since with device A engaged thereon as described the inner end portion of said tool B is inserted into the cervical canal through the external uterine orifice d and gently directed therethrough with the walls of said canal c having a compressing effect upon the arms or branches of device A causing same to be bent downwardly or toward the normally outer end of tool B. After tool B has been moved so as to introduce the said arms or branches of device A into the uterus the said arms or branches are thus permitted through the inherent bias to return to normal condition and with their edges firmly but gently abutting the confronting portions of the uterine wall for retention thereby. The movement of tool B is continued until the upper end of device A is brought into contact with the endometrium at the upper end of uterus U and all such inserting movement is then discontinued. At this juncture device A is firmly held by the gripping effect of the uterine walls upon said arms or branches so that by a tilting movement as directed toward the rear of the uterus engagement is lost between said tool guides 32 and the erstwhile embraced portion of stem 1 thereby freeing tool B for withdrawing action as the same is moved outwardly relatively along stem 1 with reverse passage through cervical canal c. During such removing action thread-like portion 3 of stem 1 travels relatively along chamber 24, through opening 30, with hook 4 being thus presented within the vagina below orifice d.

It will accordingly be seen that the curvature of the normally upper or inner end of tool B is such as to permit of but limited axial tilting of tool B to bring about the requisite disengagement between same and device A so as to free tool B for facile and nondiscomforting withdrawal.

The ultimate withdrawing of device A from the uterus after serving the intended function, such as, for instance, producing expulsion of a fertilized ovum, is easily brought about by the simple procedure of gripping hook 4 and pulling device A through uterus U and cervical canal c with such passage being facilitated as described by the upper or reverse folding of arms or branches 9,9', etc. as within the condition shown in FIG. 4.

Having described our invention, what we claim and desire to obtain by Letters Patent is 1. An intrauterine device comprising a stem, a plurality of arms integrally formed with said stem and projecting from opposite sides thereof, the stem-remote ends of said arms being free, there being a line of integration of each of said arms with said stem about which the respective arms are flexible, said arms being biased for normally presenting the longitudinal axes thereof at an angle of less than 90° to the longitudinal axis of said stem and within the plane of said stem, the line of integration of each arm forming an angle of less than 90° with the longitudinal axis of said stem whereby upon flexure the outer portions of said arms will depart from the plane of said stem.

2. An intrauterine device as defined in claim 1 and further characterized by said stem in the portion thereof adjacent said arms having opposed side faces, said arms extending from said opposite side faces, and each of said arms being relatively flat.

3. An intrauterine device as defined in claim 2 and further characterized by said arms being in paired relationship with there being a multiplicity of such pairs, said paired arms being so related that the same are of decreasing extent progressing from the proximate end of said stem.

4. An intrauterine device as defined in claim 3 and further characterized by the said arms having maximum extent being located at the end extremity of said stem remote from said relatively thin elongate portion, said stem further having a zone of thickness reduced relative to the portion adjacent to said arms between said portion and the thin elongate portion.

5. An intrauterine device as defined in claim 4 and further characterized by their being a hook formed at the end of said thin elongate portion.

6. In combination with an intrauterine device comprising a stem having a relatively thick portion adjacent one end, a relatively thin elongated portion at the opposite end, and an intervening portion of intermediate thickness, there being arms projecting laterally on opposite sides of said thick stem portion, a tool for detachably engaging said device for positioning of the same comprising an elongated rigid body, there being a handle formed at one end of said body, said body in its handle remote portion having a narrow chamber dimensioned for receiving said intrauterine device thin elongate portion, there being an end aperture in said body opening into said chamber at the end thereof remote from said handle, said aperture being of slightly greater cross section than said intrauterine device intermediate portion for acceptance of the same, a tongue extending from said tool body endwise from said aperture and transversely spaced apart guide components formed on the portion of said tongue remote from said aperture for defining a passageway therebetween substantially aligned with said aperture, said guide components being spaced apart for accepting threbetween the thick portion of said stem between adjacent arms.

7. An intrauterine device as defined in claim 1 and further characterized by the angle developed by said line of integration of each arm and said stem being within the range of 30° to 50°.

8. An intrauterine device as defined in claim 1 and further characterized by said stem incorporating a relatively thin elongate portion remote from said arms.

9. For use with an intrauterine device a tool comprising an elongated rigid body, there being a handle formed at one end of said body, said body having a narrow elongated chamber formed on its end portion remote from said handle, there being a first aperture in said body communicating with said chamber in the portion thereof remote from said handle, a tongue extending endwise from said body adjacent said end aperture, and a pair of opposed guide components formed on the end extremity of said tongue remote from said first aperture, said guide components being spaced apart transversely of said body with the intervening spacing defining a passage therebetween substantially aligned with said first aperture.

10. For use with an intrauterine device a tool as defined in claim 9 and further characterized by said tool having an axially rectilinear stem between said handle and the portion thereof containing said chamber, said chamber containing portion being lengthwise curvilinear.

11. For use with an intrauterine device a tool as defined in claim 9 and further characterized by said chamber-containing portion having a second aperture communicating with said chamber in its handle-proximate portion, the plane of the opening of said second aperture being substantially normal to the plane of the opening of said first aperture.

12. For use with an intrauterine device a tool as defined in claim 9 and further characterized by said guide components being presented within a plane at an angle of less than 180° to the plane of the proximate portion of said tongue.

13. For use with an intrauterine device a tool as defined in claim 9 and further characterized by said chamber-containing portion being lengthwise curvate.

* * * * *